(12) United States Patent
Kole et al.

(10) Patent No.: US 12,257,292 B2
(45) Date of Patent: Mar. 25, 2025

(54) ENHANCED DELIVERY OF ANTIOXIDANTS FOR TREATMENT OF CENTRAL NERVOUS SYSTEM DISORDERS INVOLVING OXIDATIVE STRESS

(71) Applicant: Beyond Barriers Therapeutics, Inc., Glencoe, IL (US)

(72) Inventors: Ryan Kole, Glencoe, IL (US); John Marshall, Chicago, IL (US); Meriel Owen, New York, NY (US)

(73) Assignee: BEYOND BARRIERS THERAPEUTICS, INC., Glencoe, IL (US)

( * ) Notice: Subject to any disclaimer, the term of this patent is extended or adjusted under 35 U.S.C. 154(b) by 82 days.

(21) Appl. No.: 18/082,379

(22) Filed: Dec. 15, 2022

(65) Prior Publication Data

US 2023/0118328 A1   Apr. 20, 2023

Related U.S. Application Data (60) Division of application No. 16/859,722, filed on Apr. 27, 2020, now Pat. No. 11,612,642, which is a continuation-in-part of application No. PCT/US2018/057983, filed on Oct. 29, 2018.

(60) Provisional application No. 62/578,061, filed on Oct. 27, 2017.

(51) Int. Cl.
| | |
|---|---|
| A61K 9/00 | (2006.01) |
| A61K 31/122 | (2006.01) |
| A61K 31/16 | (2006.01) |
| A61K 31/198 | (2006.01) |
| A61K 31/40 | (2006.01) |
| A61K 31/573 | (2006.01) |
| A61K 31/724 | (2006.01) |
| A61K 38/22 | (2006.01) |
| A61K 38/44 | (2006.01) |
| A61K 38/48 | (2006.01) |
| A61K 45/06 | (2006.01) |

(52) U.S. Cl.
CPC ........ *A61K 38/4886* (2013.01); *A61K 9/0043* (2013.01); *A61K 31/122* (2013.01); *A61K 31/16* (2013.01); *A61K 31/198* (2013.01); *A61K 31/40* (2013.01); *A61K 31/573* (2013.01); *A61K 31/724* (2013.01); *A61K 38/22* (2013.01); *A61K 38/446* (2013.01); *A61K 45/06* (2013.01)

(58) Field of Classification Search
CPC .................... A61K 31/198; A61K 9/0043
See application file for complete search history.

(56) References Cited

U.S. PATENT DOCUMENTS

| | | |
|---|---|---|
| 2006/0039995 A1 | 2/2006 | Frey et al. |
| 2006/0099244 A1 | 5/2006 | Guilford |
| 2007/0078117 A1 | 4/2007 | Hoffman et al. |
| 2008/0107756 A1 | 5/2008 | Satow |
| 2014/0050718 A1 | 2/2014 | Thorne et al. |
| 2014/0187631 A1 | 7/2014 | Kpoke et al. |
| 2015/0011626 A1 | 1/2015 | McGavern et al. |
| 2017/0174623 A1 | 6/2017 | Ott |
| 2017/0202797 A1 | 7/2017 | Kopke et al. |
| 2018/0344678 A1 | 12/2018 | Ratan et al. |

OTHER PUBLICATIONS

Dodd et al., Expert Opinion on Biological Therapy, 2008, 8(12), p. 1955-1962. (Year: 2008).*
FDA Guidance for Industry on Container Closure Systems for Packaging Human Drugs and Biologics, May 1999, 56 pages. (Year: 1999).*
Kupper et al., Journal of Travel Medicine, 2006, 13(1), p. 35-47. (Year: 2006).*
"CETYLEV (acetylcysteine) Prescribing Information", Alpex Pharma SA, Rev., Apr. 2017.
Extended European Search Report for EP Application No. 18871445. 5, dated Jul. 21, 2021, 4 pages,.
"International Preliminary Report on Patentability in pending application PCT/US2018/057983", Jan. 18, 2019.
"International Search Report and Written Opinion in pending application PCT/US18/57983", Jan. 18, 2019.
"Roxane Laboratories, Inc., Acetylcysteine Solution, USP Description and Dosage Information", Mar. 2007.
Abou-Abbass, et al., "Deciphering glycomics and neuroproteomic alterations in experimental traumatic brain injury: Comparative analysis of aspirin and clopidogrel treatment", Abou-Abbass et al., Electrophoresis, 2016, 37, p. 1562-1576. (Year: 2016).
Chiew, et al., "Interventions for paracetamol (acetaminophen) overdose", Cochrane Database of Systematic Reviews, Issue 2. Art. No. CD003328 DOI: 10.1002/14651858.CD003328.pub3., Feb. 23, 2018.
Eakin, et al., "Efficacy of N-Acetyl Cysteine in Traumatic Brain Injury", PLoS ONE, vol. 9, No. 4, Article No. e90617doi:10.1371/joumal.pone.0090617, 2014.
Hoffer, et al., "Amelioration of Acute Sequelae of Blast Induced Mild Traumatic Brain Injury by N-Acetyl Cysteine: A Double-Blind, Placebo Controlled Study", PLoS ONE, vol. 8, No. 1, Article No. e54163.doi: 10.1371/journal.pone_0054163.
Hoffer, et al., "Repositioning drugs for traumatic brain injury N-acetyl cysteine and Phenserine", Journal of Biomedical Science, vol. 24, Article No. 71, 2017.
Kanayama, et al., "Lung Inflammation Stalls Th17-Cell Migration en route to the Central Nervous System During The Development Of Experimental Autoimmune Encephalomyelitis", International Immunology, vol. 28, No. 9, Sep. 2016, pp. 463-469.

(Continued)

*Primary Examiner* — Jonathan S Lau
(74) *Attorney, Agent, or Firm* — Neal, Gerber & Eisenberg LLP (57) ABSTRACT

The present disclosure generally relates to methods and formulations for treating central nervous system (CNS) disorders. The present disclosure involves intranasal delivery of at least one antioxidant compound, allowing for effective treatment of a central nervous system disorder such as traumatic brain injury or stroke.

19 Claims, 1 Drawing Sheet

(56) References Cited

OTHER PUBLICATIONS

Mischley, Laurie K., et al., "A randomized, double-blind phase I/IIa study of intranasal glutathione in Parkinson's disease", Movement Disorders : Official Journal of the Movement Disorder, John Wiley & Sons, Inc, US 9 vol. 30, No. 12 Sep. 30, 2015 (Sep. 30, 2015), pp. 1696-1701, XP009528579, ISSN: 1531-8257, DOI: 10.1002/MDS.26351.

Ouyang, et al., "Successful bystander-administered intranasal naloxone reversal of opioid overdose between two veterans: A case report", Ment Health Clin [Internet], vol. 7, No. 6, 2017, pp. 287-279.

Patel, et al., "Ganciclovir Loaded Chitosan Nanoparticles: Preparation and Characterization", Journal of Nanomedicine and Nanotechnology, vol. 7, Dec. 28, 2016, pp. 1-8.

Rai, et al., "Effects of immunonutrition on biomarkers in traumatic brain injury patients in Malaysia: a prospective randomized controlled trial", BMC Anethesiology, vol. 17, Article No. 81, 2017.

Senol, et al., "N-Acetylcysteine and Selenium Modulate Oxidative Stress, Antioxidant Vitamin and Cytokine Values in Traumatic Brain Injury-Induced Rats", Neurochemical Research, vol. 39, 2014, pp. 685-692.

Zhou, et al., "Intravenous Administration of Stable-Labeled N-Acetylcysteine Demonstrates an Indirect Mechanism for Boosting Glutathione and Improving Redox Status", wileyonlinelibrary.com, 2015.

\* cited by examiner

ENHANCED DELIVERY OF ANTIOXIDANTS FOR TREATMENT OF CENTRAL NERVOUS SYSTEM DISORDERS INVOLVING OXIDATIVE STRESS

CROSS-REFERENCE TO RELATED APPLICATIONS

This application is a divisional of U.S. application Ser. No. 16/859,722, filed on Apr. 27, 2020, which is a continuation-in-part of International Application No. PCT/US 2018/057983, filed Oct. 29, 2018, which claims the benefit of U.S. Provisional Application No. 62/578,061, filed Oct. 27, 2017, the contents of which are incorporated by reference in their entirety.

FIELD OF THE INVENTION

The present disclosure is directed to formulations, methods, and kits for treatment of central nervous system (CNS) disorders.

BACKGROUND

Central nervous system (CNS) disorders are a collection of neurological diseases having various underlying causes, including trauma, degeneration, infection, and autoimmune disease. Oxidative stress resulting from high levels of reactive oxygen and reactive nitrogen species (ROS/RNS) can play a key role in the progression of many central nervous system disorders such as traumatic brain injury (TBI), Alzheimer's disease, and Parkinson's disease. For traumatic brain injury disorders, damage from the injury is generally divided into primary injuries, a direct result of the impact itself, and secondary injuries, biochemical and cellular events that occur over the ensuing hours and days and exacerbate the initial insult. While the exact mechanisms of this secondary injury are complex, substantial previous work has shown that oxidative stress, resulting from high levels of reactive oxygen species and reactive nitrogen species (ROS/RNS), plays a key role in pathology developing during the period of secondary injury. As a result, a number of research studies have focused on the use of antioxidants as therapeutic agents to reduce ROS/RNS species. Preclinical studies across disparate animal models have had some success in using antioxidant therapies for central nervous system disorders such as traumatic brain injury.

Traumatic brain injury is widely recognized as a public health issue for which there is no current effective pharmaceutical therapy. Statistics from the Centers for Disease Control (CDC) show that 2.5 million emergency room visits a year are due to traumatic brain injury. However, in spite of widespread interest, investment and a number of promising preclinical and initial clinical stage studies, every pharmacological agent that has advanced to phase III clinical trials for traumatic brain injury has failed. For instance, despite more than 20 preclinical studies showing that erythropoietin improves outcome following traumatic brain injury, in at least one large multi-center randomized controlled trial, erythropoietin did not reduce the number of patients with severe neurological dysfunction (GOS-E level 1-4) or increase the incidence of deep venous thrombosis of the lower limbs. Nichol et al., "Erythropoietin in traumatic brain injury (EPO-TBI): a double-blind randomised controlled trial", The Lancet, Vol. 386, No. 10012, p 2499-2506 (2015). A clinical study conducted on 81 active duty service members was said to demonstrate that orally administered N-acetylcysteine (NAC) had beneficial effects on the severity and resolution of sequelae of blast induced mild traumatic brain injury. Hoffer et al., "Amelioration of acute sequelae of blast induced mild traumatic brain injury by N-acetyl cysteine: a double-blind, placebo controlled study", PLoS One. 2013; 8(1):e54163.

NAC has been approved by the Food and Drug Administration for other indications. For example, Mucomyst (acetylcysteine solution, USP) was approved as adjuvant therapy for patients with abnormal, viscid, or inspissated mucous secretions in various conditions. Acetadote (acetylcysteine) injection for intravenous use and Cetylev (acetylcysteine) effervescent tablets for oral solution have been approved for acetaminophen overdose to prevent or lessen hepatic injury.

Success in clinical trials for traumatic brain injury is believed to be elusive in part due to patient heterogeneity, wide variation in injury severity, and differences in underlying pathology between patients. Treatments that are initially successful in the relatively controlled environment of a preclinical animal study often fail once faced with the less controlled environment of a clinical trial in a hospital setting.

SUMMARY OF THE INVENTION

In an embodiment, the present disclosure provides a method of treating a central nervous system (CNS) disorder. The method comprises intranasally administering to a subject an effective amount of at least one antioxidant compound or a pharmaceutically acceptable salt thereof.

In another embodiment, the present disclosure provides a method of treating a traumatic brain injury (TBI). The method comprises co-administering to a subject an effective amount of at least one pharmaceutical compound (for example, an antioxidant compound or a pharmaceutically acceptable salt thereof) and matrix metallopeptidase 9 (MMP-9) or a biologically active fragment or variant thereof.

In another embodiment, the present disclosure provides a pharmaceutical formulation for treating a central nervous system (CNS) disorder. The pharmaceutical formulation comprises at least one antioxidant compound or a pharmaceutically acceptable salt thereof and matrix metallopeptidase 9 (MMP-9) or a biologically active fragment or variant thereof.

In another embodiment, the present disclosure provides a kit for treating a subject having a central nervous system (CNS) disorder. The kit comprises (a) at least one antioxidant compound or a pharmaceutically acceptable salt thereof, and (b) an intranasal delivery device.

In another embodiment, the present disclosure provides a kit for treating a subject having a central nervous system (CNS) disorder. The kit comprises (a) at least one antioxidant compound or a pharmaceutically acceptable salt thereof, and (b) matrix metallopeptidase 9 (MMP-9) or a biologically active fragment or variant thereof.

These and other features and advantages of the present formulations and methods will be apparent from the following detailed description, in conjunction with the appended claims.

DEFINED TERMINOLOGY

It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

The terms "intranasal administration" and "intranasal delivery" mean that a pharmaceutical compound or pharmaceutically acceptable salt thereof, a biologically active fragment or variant thereof, or a formulation comprising any of the foregoing is administered to a subject through the nasal cavity or passes through nasal mucosa or epithelium or delivered to any portion of the nasal cavity.

The terms "treat", "treating", and "treatment" refer to a method of alleviating or abrogating a condition, disorder, or disease and/or the attendant symptoms thereof.

The term "effective amount" or "therapeutically effective amount" means a sufficient amount of the compound to treat or ameliorate a condition, disorder, or disease. When used in a medical treatment, an effective amount of one of the present compounds can be employed in pure form or, where such forms exist, in a pharmaceutically acceptable salt. Alternatively, the compound can be administered as a pharmaceutical formulation containing the compound of interest in combination with one or more pharmaceutically acceptable carriers.

The term "subject" includes humans and other primates as well as domesticated and semi-domesticated animals including, but not limited to, poultry, honeybees, cows, sheep, goats, pigs, horses, dogs, cats, rabbits, rats, mice, and the like.

The term "co-administration", as used herein, encompasses administration of two or more agents to a subject so that both agents and/or their metabolites are present in the subject at the same time. Co-administration includes simultaneous administration in separate formulations, administration at different times in separate formulations, or administration in a formulation in which both agents are present.

The term "delivery agent" refers to a moiety capable of enhancing the delivery of a pharmaceutical drug to the central nervous system of a subject. Delivery of a pharmaceutical drug may be enhanced by various mechanisms including an increase in transport, diffusion, or stability of the pharmaceutical drug. In some embodiments, the delivery agent increases transport of a pharmaceutical compound from the nasal epithelium to the central nervous system.

As used in the specification and appended claims, and in addition to their ordinary meanings, the terms "substantial" or "substantially" mean to within acceptable limits or degree to one having ordinary skill in the art. For example, "substantially cancelled" means that one skilled in the art considers the cancellation to be acceptable.

As used in the specification and the appended claims and in addition to its ordinary meaning, the terms "approximately" and "about" mean to within an acceptable limit or amount to one having ordinary skill in the art. The term "about" generally refers to plus or minus 15% of the indicated number. For example, "about 10" may indicate a range of 8.5 to 11.5. For example, "approximately the same" means that one of ordinary skill in the art considers the items being compared to be the same.

Unless defined otherwise, all technical and scientific terms used herein have the same meaning as commonly understood by those working in the fields to which this disclosure pertain.

DETAILED DESCRIPTION

The present disclosure generally relates to formulations and methods for treatment of central nervous system (CNS) disorders that enhance the delivery of pharmaceutical compounds to the central nervous system. A major barrier to pharmacological treatment of brain disorders is the blood brain barrier, a network of endothelial cells coupled by tight junctions that govern solution flow and movement of compounds in and out of the brain parenchyma and that consequently reduces the effective concentration of a systemically administered compound able to reach the brain. Treatment of central nervous system disorders such as traumatic brain injury (TBI) may be enhanced using intranasal administration of pharmaceutical compounds, resulting in efficient brain delivery of the pharmaceutical compound. For example, pairing an antioxidant such as N-acetylcysteine (NAC) with intranasal administration that specifically targets the nasal epithelium may result in effective delivery of the antioxidant compound to the brain. Without wishing to be bound by any particular theory, direct nose to brain transport is thought to be possible via neural connections that travel from the central nervous system across the cribriform plate into the olfactory region of the nasal cavity. These olfactory cells pass through the nasal epithelium, which seals the nasal cavity from the central nervous system. As a result, in some embodiments, intranasal administration of pharmaceutical compounds such as antioxidant compounds produces higher therapeutic outcomes than other delivery routes.

The present disclosure provides ways to increase the robustness of treatments through rational design of improved pharmaceutical formulations or delivery methods, where others might have abandoned promising treatments. In particular, rapid and targeted delivery of antioxidant compounds following injury may arrest or diminish toxic oxidative cascades, resulting in effective treatment of the targeted central nervous system disorder.

In some embodiments, the present methods and formulations may increase levels or concentrations of glutathione in a subject's brain in addition to or instead of increasing the level or concentration of a compound in either the brain or vasculature, if that compound is intranasally administered to the subject. Without wishing to be bound by any particular theory, an administered antioxidant compound may undergo conversion to cysteine in the subject's vasculature, followed by cysteine uptake across the blood brain barrier. In this manner, cysteine required for glutathione synthesis in the brain may be facilitated. In some embodiments, N-acetylcysteine is intranasally administered to a subject in order to increase a level of glutathione in the subject's brain.

The present disclosure also relates to treatment of central nervous system disorders by administering a pharmaceutical agent in combination with a delivery agent to enhance transport of the pharmaceutical compound to neural tissue. It has been discovered that agents such as matrix metallopeptidase 9 (MMP-9) may be employed to enhance the delivery of pharmaceutical compounds (e.g., an antioxidant) to neural tissue. Other delivery agents such as chitosan loaded nanoparticles, lipophilic micelles, or liposomal carriers may be used to enhance delivery of a pharmaceutical compound to neural tissue as well.

In an embodiment, the present disclosure provides a method of treating a central nervous system disorder. The method comprises intranasally administering to a subject an effective amount of at least one antioxidant compound or a pharmaceutically acceptable salt thereof.

In some embodiments, the antioxidant compound is a small molecule. In some embodiments, the antioxidant compound is an enzyme. In some embodiments, the antioxidant compound is lipid soluble. In some embodiments, the antioxidant compound is water-soluble.

In some embodiments, the antioxidant compound is N-acetylcysteine. In some embodiments, the antioxidant compound is glutathione or a derivative thereof. In some embodiments, the antioxidant compound is coenzyme Q10. In some embodiments, the antioxidant compound is superoxide dismutase (SOD).

In some embodiments, the antioxidant compound is a pyrrolopyrimidine compound. In some embodiments, the antioxidant compound is a ubiquinone compound. In some embodiments, the antioxidant compound is a lazaroid compound.

In some embodiments, the antioxidant compound is selegiline. In some embodiments, the antioxidant compound is idebenone. In some embodiments, the antioxidant compound is probucol. In some embodiments, the antioxidant compound is tirilazad. In some embodiments, the antioxidant compound is memantine. In some embodiments, the antioxidant compound is ebselen. In some embodiments, the antioxidant compound is lipoic acid. In some embodiments, the antioxidant compound is vitamin E. In some embodiments, the antioxidant compound is vitamin C. In some embodiments, at least one antioxidant compound is a mixture of two or more of the aforementioned antioxidant compounds.

In some embodiments, the method further comprises administering a delivery agent to the subject. The delivery agent can be administered to the subject before, during or after the administration of the antioxidant compound. In some embodiments, a delivery agent is administered simultaneously with the antioxidant compound, such as when the antioxidant compound and the delivery agent are mixed in the same pharmaceutical formulation. In some embodiments, a delivery agent is administered before the administration of the antioxidant compound, for example, no more than about 15 seconds before, alternatively no more than about 30, 60, 90 or 120 seconds before, alternatively between 1 second and 10 minutes before the administration of the antioxidant compound.

In some embodiments, the method further comprises administering matrix metallopeptidase 9 (MMP-9) or a biologically active fragment or variant thereof. MMP-9 is an enzyme of the zinc-metalloproteinase family and is a member of a large family of metallopeptidases. MMP-9 is expressed at the olfactory epithelium where it plays a key role in the migration of newborn olfactory neurons. Use of matrix metallopeptidase 9 or a biologically active fragment or variant thereof can enhance the delivery of antioxidant compounds (e.g., N-acetylcysteine) to the central nervous system. Without wishing to be bound by any particular theory, it is believed that MMP-9 renders the nasal epithelium more permeable to pharmaceutical drugs by degrading type IV collagen. This degradation is believed to result in improved absorption of the pharmaceutical drug.

In some embodiments, the method further comprises administering an MMP-9 fragment or variant. In some embodiments, the MMP-9 fragment or variant is a chimeric protein comprising a biologically active fragment or variant of MMP-9.

Matrix metallopeptidase 9 may exist as various isoforms or variants. For example, the MMP-9 protein may have different lengths, sequences, or fold structures. In some embodiments, the MMP-9 comprises an MMP-9 fragment. In some embodiments, the method comprises administering at least one fragment of a MMP-9 protein. In some embodiments, the method comprises administering a fragment having a substantial sequence identity with the full-length MMP-9 protein. In some embodiments, the fragment comprises at least about 60%, at least about 75%, at least about 85%, at least about 90%, at least about 95%, at least about 96%, at least about 97%, at least about 98%, at least about 99%, at least about 99.5%, or about least about 99.9% of the sequence of full-length MMP-9 protein. However, the MMP-9 fragment may have any length consistent with the uses described herein.

In some embodiments, the MMP-9 fragment or variant thereof has at least 50% activity of the wild type version of MMP-9. Thus, in some embodiments, the MMP-9 fragment or variant thereof has a least 50%, at least 60%, at least 70%, at least 75%, at least 80%, at least 85%, at least 90%, at least 95%, at least 98%, at least 99%, or at least 99.9% activity of the wild type version of MMP-9. In some embodiments, the method further comprises administering a functionally equivalent fragment of MMP-9 (i.e., at least 75% activity of the wild type version of MMP-9). In some embodiments, the method comprises administering a MMP-9 having a full-length human MMP-9 protein.

The MMP-9 or biologically active fragment or variant thereof may be obtained from any suitable source. In some embodiments, the matrix metallopeptidase 9 or biologically active fragment or variant thereof is human-derived. In some embodiments, the matrix metallopeptidase 9 or biologically active fragment or variant thereof is murine-derived. In some embodiments, the matrix metallopeptidase 9 or biologically active fragment or variant thereof is rabbit-derived.

In some embodiments, MMP-9 or a biologically active fragment or variant thereof is administered before at least one antioxidant compound is administered to the subject. In some embodiments, MMP-9 or a fragment of variant thereof is administered simultaneously with the at least one antioxidant compound. In some embodiments. MMP-9 is administered less than about 5 minutes, less than about 10 minutes, less than about 15 minutes, less than about 20 minutes, less than about 30 minutes, less than about 1 hour, or less than about 2 hours prior to administering the at least one antioxidant compound to the subject. In some embodiments, MMP-9 is administered from about 1 minute to about 2 hours, from about 1 minutes to about 1 hour, from about 1 minute to about 30 minutes, from about 1 minute to about 20 minutes, or from about 1 minute to about 10 minutes before the at least one antioxidant is administered to the subject. In some embodiments, MMP-9 or a biologically active fragment or variant thereof is intranasally administered to the subject.

The matrix metallopeptidase 9 or a biologically active fragment or variant thereof may be used in any suitable amount. In some embodiments, MMP-9 or a biologically active fragment or variant thereof is in an amount of from about 0.001 nM to about 100 μM of a pharmaceutical formulation. Thus, in some embodiments, MMP-9 or a biologically active fragment or variant thereof is used in an amount of from about 0.001 nM to about 100 μM, from about 0.001 nM to about 50 μM, from about 0.001 nM to about 20 μM, from about 0.001 nM to about 10 μM, from about 0.001 nM to about 1 μM, from about 0.001 nM to about 500 nM, or from about 0.001 nM to about 100 nM of a pharmaceutical formulation. In some embodiments, MMP-9 or a biologically active fragment or variant thereof is used in an amount of at least about 15 μM, at least about 20 µM, at least about 25 µM, at least about 50 µM, at least about 75 µM, or at least about 100 µM of a pharmaceutical formulation.

Other delivery agents may be used in the present method. In some embodiments, delivery agents such as chitosan nanoparticles for mucoadhesion (e.g., pharmaceutical agent-loaded), micelles (e.g., lipophilic), or liposomal carriers such as archaeosomes, niosomes, novasomes, cyptosomes, emulsomes, and vesosomes are used to enhance delivery of the antioxidant compound to the brain. In some embodiments, the delivery agent can be an alkylsaccharide transmucosal delivery enhancement agent (such as Intravail®) which could increase the bioavailability of NAC, an absorption-enhancing water-based gel for transmucosal and transdermal drug delivery (such as Hydrogel™) or a pectin-based gelling agent (such as PecSys™) that can reduce drip and run-off.

In some embodiments, the method further comprises administering an anti-inflammatory agent to the subject. In some embodiments, the anti-inflammatory agent is a steroid. In some embodiments, the anti-inflammatory agent is a neurosteroid. In some embodiments, the anti-inflammatory agent is a lipophilic neurosteroid, a synthetic steroid, or a combination thereof. In some embodiments, the anti-inflammatory agent is progesterone.

In some embodiments, the anti-inflammatory agent is a non-steroidal compound. In some embodiments, the anti-inflammatory agent is trofinetide. In some embodiments, the anti-inflammatory agent comprises ghrelin or a variant thereof. In some embodiments, the anti-inflammatory agent is enoprofen, ibuprofen, indomethacin, naproxen, tolmetin, or a combination thereof.

In some embodiment, the anti-inflammatory agent is administered simultaneously with the at least one antioxidant compound. In some embodiments, the anti-inflammatory agent is administered prior to administering the at least one antioxidant compound to the subject. In some embodiments, the anti-inflammatory agent is intranasally administered to the subject.

In some embodiments, the method further comprises administering acetaminophen or aspirin. In some embodiment, acetaminophen or aspirin is administered simultaneously with the at least one antioxidant compound. In some embodiments, acetaminophen or aspirin is administered prior to administering the at least one antioxidant compound to the subject.

In some embodiments, the method further comprises administering to a subject an inhibitor of a purinergic receptor. In some embodiments, the purinergic receptor is P2X4, P2X7, P2Y6, or P2Y12. In some embodiments, the inhibitor of a purinergic receptor is a thienopyridine compound. In some embodiments, the inhibitor of a purinergic receptor is clopidogrel, prasugrel, ticlopidine, ticagrelor, cangreloror, or a combination thereof. In some embodiments, the inhibitor of a purinergic receptor is administered simultaneously with the at least one antioxidant compound. In some embodiments, the inhibitor of a purinergic receptor is administered prior to administering the at least one antioxidant compound to the subject. In some embodiments, the inhibitor of a purinergic receptor is intranasally administered to the subject.

In another embodiment, the present disclosure provides a method of treating a traumatic brain injury. The method comprises administering to a subject an effective amount of a pharmaceutical composition comprising at least one pharmaceutical compound and matrix metallopeptidase 9 or a biologically active fragment or variant thereof.

In some embodiments, the pharmaceutical compound is an antioxidant compound as described above. In some embodiments, the antioxidant compound is a pyrrolopyrimidine compound, ubiquinone compound, a lazaroid compound, or a combination thereof. In some embodiments, the pharmaceutical compound is N-acetylcysteine, glutathione, co-enzyme Q-10, superoxide dismutase, or a combination thereof. In some embodiments, the antioxidant compound is intranasally administered to the subject.

In some embodiments, the pharmaceutical compound is an anti-inflammatory agent as described above. For example, in some embodiments, the anti-inflammatory agent is a steroid or a non-steroidal compound. In some embodiments, the anti-inflammatory agent is a neurosteroid. In some embodiments, the anti-inflammatory agent is progesterone, trofinetide, ghrelin or a variant thereof, or a combination thereof. In some embodiments, the anti-inflammatory agent is enoprofen, ibuprofen, indomethacin, naproxen, tolmetin, or a combination thereof. The anti-inflammatory agent may be administered separately or simultaneously with the at least one antioxidant compound. In some embodiments, the pharmaceutical compound is acetaminophen or aspirin.

In some embodiments, the pharmaceutical compound is an inhibitor of a purinergic receptor as described above. In some embodiments, the purinergic receptor is selected from the group consisting of P2X4, P2X7, P2Y6, and P2Y12. In some embodiments, the inhibitor of a purinergic receptor is clopidogrel, prasugrel, ticlopidine, ticagrelor, cangreloror, or a combination thereof. The inhibitor of a purinergic receptor may be administered separately or simultaneously with the pharmaceutical composition.

Other delivery agents may be used in the present method. In some embodiments, delivery agents such as chitosan nanoparticles for mucoadhesion (e.g., pharmaceutical agent-loaded), micelles (e.g., lipophilic), or liposomal carriers such as archaeosomes, niosomes, novasomes, cyptosomes, emulsomes, and vesosomes are used to enhance delivery of the antioxidant compound to the brain. In some embodiments, the delivery agent can be an alkylsaccharide transmucosal delivery enhancement agent (such as Intravail®) which could increase the bioavailability of NAC, an absorption-enhancing water-based gel for transmucosal and transdermal drug delivery (such as Hydrogel™) or a pectin-based gelling agent (such as PecSys™) that can reduce drip and run-off.

When the subject is treated intranasally, the compounds or formulations of the present disclosure may be administered using any suitable delivery method. In some embodiments, a solution is applied directly to the nasal epithelium or to a portion of the nasal epithelium. In some embodiments, the compound or formulation is administered via a nasal spray, nasal drops, mist, gas, or an aerosol. The spray device may be a metered spray or suspension spray device. The aerosol device may be an aerosol, metered aerosol, powder aerosol, or a spray aerosol device. In some embodiments, the compound or formulation is administered as a solution, powder, or lyophilized or a rehydrated lyophilized form.

In some embodiments, a solution (e.g., an aqueous solution) is administered to a subject using an intranasal device such as a spray bottle, metered device, or an epithelium targeting device. In some embodiments, the intranasal device propels the solution or a mist of solution into the nasal cavity using air or an inert gas. In some embodiments, a nebulizer device is used to deliver the compound or formulation to the nasal epithelium of the subject. The nebulizer device may be mechanical or electrical. The nebulizer device may be a soft mist inhaler, powder nebulizer, jet nebulizer, ultrasonic wave nebulizer, or a vibrating mesh nebulizer. In some embodiments, the device has a clock or time device, which indicates to a user or caregiver when an additional dose should be administered.

The compounds or formulations of the present disclosure can be delivered to the nasal epithelium using a variety of commercially available devices. Suitable delivery devices include VersiDoser™ delivery system, Kurve Controlled Particle Dispersion™ delivery device. Fasynose® nebulizer, impel Precision Olfactory Delivery™, ViaNase™ electronic atomizer, Aptar Pharma nasal spray pump, and Optinose breath-powered nasal delivery device. Such devices may enhance delivery of a pharmaceutical compound (e.g., antioxidant compound) to the central nervous system of a subject.

In some embodiments, the neural tissue of the brain comprises a higher concentration of antioxidant compound when administered intranasally then when administered using a different method (e.g., orally or parenterally).

In another embodiment, the present disclosure provides a pharmaceutical formulation for treating a central nervous system disorder. The pharmaceutical formulation comprises at least one antioxidant compound or a pharmaceutically acceptable salt thereof and matrix metallopeptidase 9 (MMP-9) or a biologically active fragment or variant thereof. The matrix metallopeptidase 9 (MMP-9) or a biologically active fragment or variant thereof is as described above.

In some embodiments, the antioxidant compound is as described above. In some embodiments, the antioxidant compound is a small molecule. In some embodiments, the antioxidant compound is an enzyme. In some embodiments, the antioxidant compound is a pyrrolopyrimidine compound, ubiquinone compound, a lazaroid compound, or a combination thereof. In some embodiments, the pharmaceutical compound is N-acetylcysteine, glutathione, co-enzyme Q-10, superoxide dismutase, or a combination thereof. In the present disclosure, references to the "antioxidant compound" should be understood to also refer to pharmaceutically acceptable salts, hydrates, solvates, and prodrugs of antioxidant compounds.

In some embodiments, the pharmaceutical formulation further comprises an anti-inflammatory agent as described above. For example, in some embodiments, the anti-inflammatory agent is a steroid or a non-steroidal compound. In some embodiments, the anti-inflammatory agent is progesterone, trotinetide, ghrelin or a variant thereof, or a combination thereof. In some embodiments, the anti-inflammatory agent is enoprofen, ibuprofen, indomethacin, naproxen, tolmetin, or a combination thereof.

In some embodiments, the pharmaceutical formulation further comprises an inhibitor of a purinergic receptor as described above. In some embodiments, the purinergic receptor is selected from the group consisting of P2X4, P2X7, P2Y6, and P2Y12. In some embodiments, the inhibitor of a purinergic receptor is clopidogrel, prasugrel, ticlopidine, ticagrelor, cangreloror, or a combination thereof.

Other delivery agents may be present in the pharmaceutical formulation. In some embodiments, delivery agents such as chitosan nanoparticles for mucoadhesion (e.g., pharmaceutical agent-loaded), micelles (e.g., lipophilic), or liposomal carriers such as archaeosomes, niosomes, novasomes, cyptosomes, emulsomes, and vesosomes are used to enhance delivery of the antioxidant compound to the brain. In some embodiments, the delivery agent can be an alkylsaccharide transmucosal delivery enhancement agent (such as Intravail®) which could increase the bioavailability of NAC, an absorption-enhancing water-based gel for transmucosal and transdermal drug delivery (such as Hydrogel™) or a pectin-based gelling agent (such as PecSys™) that can reduce drip and run-off.

In some embodiments, the pharmaceutical formulation comprises one or more formulation components, including excipients that aid permeation or are suitable for use in intranasal delivery. Some examples of formulation components include pharmaceutically acceptable carriers are sugars, such as lactose, glucose and sucrose; starches such as corn starch and potato starch; cellulose and derivatives such as sodium carboxymethyl cellulose, ethyl cellulose and cellulose acetate; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol: esters such as ethyl oleate and ethyl laurate; agar; buffering agents such as magnesium hydroxide and aluminum hydroxide; alginic acid; pyrogen free water; isotonic saline; solvents such as ethyl alcohol; and buffers such as phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be included in the present formulations.

In some embodiments, the pharmaceutical formulation comprises and/or the delivery device comprises a fragrance, chemical additive, or other component that would alleviate the odor coming from NAC. Additionally, a sugar or sweetener can be added to alleviate the odor coming from NAC. Additionally NAC can be complexed with a cyclodextrin or ion exchange resin. NAC can be incorporated into the cavity of a cyclodextrin, for instance, (2-Hydroxypropyl)-β-cyclodextrin (HP-β-CyD) also known as (2-hydroxypropyl) beta-cyclodextrin (HPBCD).

In some embodiments, the pharmaceutical formulation comprises an analgesic or flavoring compound to assist the subject's intranasal acceptance of the formulation and decrease the chances of a sneeze or other type of involuntary intranasal rejection. Suitable analgesics include but are not limited to lidocaine, pethidine, tramadol, metamizole, codeine and diclofenac. In some embodiments, the present methods and formulations further comprise an agent for enhancing delivery or and/or alleviating odor from the at least one antioxidant compound or salt thereof. For example, the agent can comprise a cyclodextrin compound in an amount effective to enhance delivery of or alleviate odor from the at least one antioxidant compound or salt thereof. An exemplary cyclodextrin compound is (2-hydroxypropyl) beta-cyclodextrin (HPBCD). In some embodiments, the agent for enhancing delivery or and/or alleviating odor is administered to the subject before administering the at least one antioxidant compound or salt thereof. Alternatively, the agent is mixed with and/or administered simultaneously with the antioxidant agent. In some embodiments, the agent is administered once in one nostril of the subject, or once in each nostril of the subject.

In some embodiments, the pharmaceutical formulation comprises an additional antioxidant to prevent NAC oxidation: adipic acid, ascorbic acid, ascorbyl palmitate, butylated hydroxyanisole, butylated hydroxytoluene, citric acid, dithiothreitol, glutamic acid, propyl gallate, sodium formaldehyde sulfoxylate, sodium metabisulfite, sodium sulfite, sodium thiosulfate, tartaric acid, thioglycerol, throurea, tocopherols, p-toluene sulfonic acid. Or a combination of hydrogen atom donor and metal chelator: citric acid, EDTA, fumaric acid and malic acid can be used to reduce NAC oxidation. In some embodiments, an intranasal delivery device holding the antioxidant compound or salt would be configured to reduce or minimize the oxidation of the antioxidant compound by storing it under an inert gas such as Argon or Nitrogen. In some embodiments, NAC solution can be kept at low pH and/or stored in packaging with low oxygen permeability such as borosilicate glass, high density polyethylene (HDPE), polypropylene (PP), polystyrene (PS), polyvinylchloride (PVC), polycarbonate (PC), unoriented polyethyelene terephthalate (PET), or oriented PET.

In some embodiments, the pharmaceutical formulation is an aqueous solution. In some embodiments, the pharmaceutical formulation is a saline solution. In some embodiments, the pharmaceutical formulation further comprises a buffer. In some embodiments, the pharmaceutical formulation comprises phosphate buffered saline (PB5) solution.

In another embodiment, the present disclosure provides a kit for treating a subject having a central nervous system (CNS) disorder. The kit comprises (a) at least one antioxidant compound or a pharmaceutically acceptable salt thereof, and (b) an intranasal delivery device.

In another embodiment, the present disclosure provides a kit for treating a subject having a central nervous system disorder. The kit comprises (a) at least one antioxidant compound or a pharmaceutically acceptable salt thereof, and (b) matrix metallopeptidase 9 (MMP-9) or a biologically active fragment or variant thereof. In some embodiments, the kit further comprises a means for intranasally delivering (a) and (b) as described above. The matrix metallopeptidase 9 (MMP-9) or a biologically active fragment or variant thereof is as described above.

In some embodiments, the kit comprises a "pre-mixed" container comprising a formulation comprising (a) at least one antioxidant compound or a pharmaceutically acceptable salt thereof, and (b) matrix metallopeptidase 9 or a biologically active fragment or variant thereof. In some embodiments, the "pre-mixed" container is an intranasal delivery device such as a nebulizer or sprayer. In some embodiments, the kit comprises at least one prefilled intranasal delivery device. In some embodiments, the kit comprises at least two prefilled intranasal delivery devices. In some embodiments, the kit comprises at least three prefilled intranasal delivery devices. In some embodiments, the kit comprises at least four prefilled intranasal delivery devices. In some embodiments, the kit comprises at least five prefilled intranasal delivery devices.

In some embodiments, the pharmaceutical formulation is pre-loaded into an intranasal delivery device which is included, along with appropriate usage instructions, as part of a ready-to-use kit in a case. For example, an outer carrying case can be adapted for carrying a plurality of containers and instructions for using the components of the kit, such as by its arrangement of pockets and clips. The case can be adapted to keep the pharmaceutical formulation and/or additional chemicals stable. In some embodiments, the case is adapted to protect the pharmaceutical formulation from severe weather or conditions, i.e., rain, snow, extreme cold, extreme heat, humidity, dryness and/or to protect the pharmaceutical formulation and the intranasal delivery device from physical damage such as shaking or being dropped. In some embodiments, the kit or case is adapted to be stored in a soldier's backpack and be readily available in any environment or conditions.

In some embodiments, the present kits comprise one or more prefilled containers with a pharmaceutical formulation comprising at least one antioxidant compound or salt thereof. The containers can be vials, cartridges, or other containers adapted for operation with an intranasal delivery device, such as by loading, inserting, or otherwise connecting the containers to the intranasal delivery device. In some embodiments, the kit further comprises an outer carrying case for carrying the intranasal delivery device, one or more prefilled containers, and other components. The pharmaceutical formulation is pre-formulated into a number of vials or cartridges that can be loaded into an intranasal delivery device. Such vials, cartridges or other containers can be included, along with appropriate usage instructions, as part of a ready-to-use kit in an outer carrying case.

In some embodiments, the present kits comprise one or more containers with agents other than an antioxidant compound. For instance, a kit can comprise separate containers of an agent for enhancing delivery of and/or alleviating odor from an antioxidant compound. In some embodiments, the present kits comprise one or more containers that contain a fragrance or a masking agent, such as a cyclodextrin compound (e.g., (2-hydroxypropyl) beta-cyclodextrin (HPBCD)).

In some embodiments, the antioxidant compound is as described above. For example, in some embodiments, the antioxidant compound is selected from the group consisting of N-acetylcysteine, glutathione, co-enzyme Q-10, superoxide dismutase (SOD), and a combination thereof.

In some embodiments, the metallopeptidase 9 or a biologically active fragment or variant thereof is a chimeric protein or fusion protein, with the MMP-9 catalytic domain fused to a mucoadhesive peptide. In some embodiments, the matrix metallopeptidase 9 or a biologically active fragment or variant thereof comprises the full-length MMP-9 protein fused to another protein or fragment or variant thereof.

In some embodiments, the kit comprises components (a) and (b) in separate containers. Thus, in some embodiments, the kit comprises at least one antioxidant compound or a pharmaceutically acceptable salt thereof in a first container and matrix metallopeptidase 9 (MMP-9) or a biologically active fragment or variant thereof in a second container.

In some embodiments, the kit comprises instructions for using the components of the kit. In some embodiments, the kit comprises instructions for mixing the separate components, suitable conditions for the components and/or mixture, and/or suitable vessels for mixing the composition. Where a kit comprises a plurality of containers, the kit can also include instructions that direct how to use the respective containers, such as the order and timing of use. For instance, the instructions may direct the subject to administer an agent for enhancing delivery of and/or alleviating odor in one or both nostrils before the administration of an antioxidant compound, such as at a required or recommended time period before antioxidant compound administration. For example, the instructions may direct a user to administer a cyclodextrin compound such as HPBCD to one or both nostrils of a subject at least 10, 15, 30, 60 or more seconds, before administering NAC to one or both nostrils, and/or no more than 10, 5, 2 or 1 minute before administering NAC to one or both nostrils; the foregoing values can be combined to form a range. Alternatively, the instructions may direct the subject to administer an agent for enhancing delivery of and/or alleviating odor and an antioxidant compound in one or both nostrils at substantially the same time as the administration of an antioxidant compound, including by mixing together before administration.

The instructions may contain how often to apply the antioxidant compound, and/or the time for administration after an initial injury, and/or the timing of application between 1 nostril to the other if the antioxidant compound is to be administered to both nostrils. In some embodiments, the instructions include the length of treatment and how often each day it should be administered. In some embodiments, the instructions may also include dosing amounts based on a subject's age, weight and/or how severe a subject's head injury is.

In some embodiments, the kit further comprises one or more additional compounds. For example, the kit may further comprise an anti-inflammatory agent, purinergic receptor inhibitor, or another drug delivery agent such as chitosan nanoparticles for mucoadhesion (e.g., pharmaceutical agent-loaded), micelles (e.g., lipophilic), or liposomal carriers as described above. The kit may further comprise a delivery enhancing agent, a masking agent, an odor suppressing agent, a fragrance, an analgesic, or other agents. In some embodiments, the additional compounds are provided in the same or separate containers.

The formulations and methods of the present disclosure may be used to treat any central nervous system disorder. In some embodiments, the formulations and methods of the present disclosure are used to treat a central nervous system disorder involving oxidative stress. In some embodiments, the formulations and methods of the present disclosure are used to treat a central nervous system disorder resulting from injury, autoimmune disease, or a degenerative disorder. In some embodiments, the formulations and methods of the present disclosure are used to treat a traumatic brain injury. In some embodiments, the central nervous system disease is selected from traumatic brain injury (TBI), Parkinson's disease, Huntington's disease, stroke, depression, bi-polar disorder, Alzheimer's disease, and amyotrophic lateral sclerosis (ALS).

In some embodiments, the methods and compositions of the present disclosure are used to treat a neurodegenerative disorder. In some embodiments, the formulations and methods of the present disclosure are used to treat Alzheimer's disease. In some embodiments, the formulations and methods of the present disclosure are used to treat Parkinson's disease. In some embodiments, the formulations and methods of the present disclosure are used to treat Huntington's disease. In some embodiments, the formulations and methods of the present disclosure are used to treat amyotrophic lateral sclerosis (ALS). In some embodiments, the formulations and methods of the present disclosure are used to treat dementia. In some embodiments, the formulations and methods of the present disclosure are used to treat stroke.

In some embodiments, the formulations and methods of the present disclosure are used to treat multiple sclerosis (MS). In some embodiments, the formulations and methods of the present disclosure are used to treat epilepsy. In some embodiments, the formulations and methods of the present disclosure are used to treat a central nervous system disorder resulting from a stroke, tumor, or an infection. In some embodiments, the formulations and methods of the present disclosure are used to treat autism, obsessive compulsive disorder ((M)), schizophrenia, addiction, or depression.

In some embodiments, the formulations and methods of the present disclosure are used to treat hearing loss, such as conductive hearing loss, sensorineural hearing loss, or mixed hearing loss. For example, the formulations and methods can be used to treat noise induced hearing loss. The hearing loss can be caused by or accompanying traumatic brain injury, or can be independent of traumatic brain injury.

In some embodiments, the formulations and methods of the present disclosure are used to treat blast-induced hearing loss from an explosion such as an IED. In some embodiments, the formulations and methods of the present disclosure are used to treat age-related hearing loss (presbycusis).

The pharmaceutical compounds of the present disclosure (e.g., antioxidant compound) may be administered to a subject using any suitable dosage regimen. In some embodiments, the pharmaceutical compound is administered to a subject for at least 1 day. In some embodiments, the pharmaceutical compound is administered to a subject for at least 2 days. In some embodiments, the pharmaceutical compound is administered to a subject for at least 3 days. In some embodiments, the pharmaceutical compound is administered to a subject for at least 4 days. In some embodiments, the pharmaceutical compound is administered to a subject for at least 5 days. In some embodiments, the pharmaceutical compound is administered to a subject for at least 6 days. In some embodiments, the pharmaceutical compound is administered to a subject for at least 7 days. The pharmaceutical compound may be separately dosed or administered simultaneously with at least one anti-inflammatory agent, inhibitor of a purinergic receptor, or delivery agent (e.g., MMP-9 or a biologically active fragment or variant thereof) as described above.

In some embodiments, the pharmaceutical compound (e.g., antioxidant compound) is administered once daily. In some embodiments, two doses of pharmaceutical compound (e.g., antioxidant compound) are administered daily. In some embodiments, the pharmaceutical compound (e.g., antioxidant compound) is administered once daily for 1 to 30 days or for a longer period, such as 1 to 60 or 1 to 90 days, or for a period of 7, 14, 28, 56, or 84 days. In some embodiments, the pharmaceutical compound (e.g., antioxidant compound) is administered once daily for 5 to 7 days. In some embodiments, two doses of pharmaceutical compound (e.g., antioxidant compound) are administered daily for 5 to 7 days. The dosing regimen may depend on the half-life of the pharmaceutical compound (e.g., antioxidant compound). The pharmaceutical compound (e.g., antioxidant compound) may be separately dosed or administered simultaneously with any anti-inflammatory agent, inhibitor of a purinergic receptor, or delivery agent (e.g., MMP-9 or a biologically active fragment or variant thereof) as described above.

In some embodiments, at least one antioxidant compound is administered to a subject having a traumatic brain injury. Rapid and targeted delivery of the antioxidant compound following traumatic brain injury may arrest or reduce oxidative cascade reactions in the brain of the subject. In some embodiments, the antioxidant compound is administered to the subject immediately after traumatic brain injury. In some embodiments, the antioxidant compound is administered to the subject within 5 minutes, 10 minutes, 15 minutes, or 30 minutes of traumatic brain injury. In some embodiments, the antioxidant compound is administered to the subject within 1 hour of traumatic brain injury. In some embodiments, the antioxidant compound is administered to the subject within 2 hours of traumatic brain injury. In some embodiments, the antioxidant compound is administered to the subject within 4 hours of traumatic brain injury. In some embodiments, the antioxidant compound is administered to the subject within 6 hours of traumatic brain injury. In some embodiments, the antioxidant compound is administered to the subject within 12 hours of traumatic brain injury. In some embodiments, the antioxidant compound is administered to the subject within 16 hours of traumatic brain injury. In some embodiments, the antioxidant compound is administered to the subject within 24 hours of traumatic brain injury. In some embodiments, the antioxidant compound is administered to the subject within 2 days of traumatic brain injury. The antioxidant compound may be separately dosed or administered simultaneously with any anti-inflammatory agent, inhibitor of a purinergic receptor, or delivery agent (e.g., MMP-9 or a biologically active fragment or variant thereof) as described above. Intranasally administering the antioxidant compound (e.g., by a first responder), alone or in combination with at least one pharmaceutical or delivery agent, may allow for immediate treatment of a subject suffering from a traumatic brain injury.

The pharmaceutical compounds (e.g., antioxidant compound) of the present disclosure can be administered in any suitable amount to treat a central nervous system disorder (e.g., traumatic brain injury). In some embodiments, the total daily dose of a pharmaceutical compound (e.g., an antioxidant compound) (administered in single or divided doses) is from about 0.001 to about 100 mg/kg (i.e., mg of the compound or salt per kg body weight). Thus, in some embodiments, the total daily dose of the antioxidant compound (administered in single or divided doses) is from about 0.001 to about 100 mg/kg, from 0.001 to about 50 mg/kg, from 0.001 to about 30 mg/kg, from 0.001 to about 20 mg/kg, or from about 0.01 to about 10 mg/kg (i.e., mg of the compound or salt per kg body weight). In some embodiments, dosage unit compositions contain such amounts or submultiples thereof to makeup the daily dose. In some embodiments, multiple doses per day may be used to increase the total daily dose, if desired. The amount of pharmaceutical compound may need to be adjusted based on severity, age, severity of concussion, weight, and/or size of the subject suffering from the central nervous system disorder (e.g., traumatic brain injury).

In some embodiments, the brain or neural tissue of a subject comprises a higher concentration of pharmaceutical compound (e.g., antioxidant compound) or salt thereof when co-administered with MMP-9 or a biologically active fragment or variant thereof than when administered in the absence of MMP-9 or a biologically active fragment or variant thereof. In some embodiments, the cerebellum of the brain of a subject comprises a higher concentration of pharmaceutical compound (e.g., antioxidant compound) when co-administered with MMP-9 or a biologically active fragment or variant thereof than when administered in the absence of MMP-9 or a biologically active fragment or variant thereof. In some embodiments, the whole brain or a region of the brain (for example, but not limited to, the brainstem and/or the cerebral spinal fluid) of a subject comprises a higher concentration of pharmaceutical compound (e.g., antioxidant compound) when co-administered with MMP-9 or a biologically active fragment or variant thereof than when administered in the absence of MMP-9 or a biologically active fragment or variant thereof. In some embodiments, the cerebral cortex of a subject comprises a higher concentration of pharmaceutical compound (e.g., antioxidant compound) when co-administered with MMP-9 or a biologically active fragment or variant thereof than when administered in the absence of MMP-9 or a biologically active fragment or variant thereof. In some embodiments, the frontal cortex of the brain of a subject comprises a higher concentration of pharmaceutical compound (e.g., antioxidant compound) when co-administered with MMP-9 or a biologically active fragment or variant thereof than when administered in the absence of MMP-9 or a biologically active fragment or variant thereof. In some embodiments, the hippocampus of the brain of a subject comprises a higher concentration of pharmaceutical compound (e.g., antioxidant compound) when co-administered with MMP-9 or a biologically active fragment or variant thereof than when administered in the absence of MMP-9 or a biologically active fragment or variant thereof. In some embodiments, the olfactory bulb of a subject comprises a higher concentration of pharmaceutical compound (e.g., antioxidant compound) when co-administered with MMP-9 or a biologically active fragment or variant thereof than when administered in the absence of MMP-9 or a biologically active fragment or variant thereof. In some embodiments, one or more of the thalamus, the basal ganglia, the cortex, the cerebellum, the brain stem, or the nuclei, or all of those regions, of the brain of a subject comprises a higher concentration of pharmaceutical compound (e.g., antioxidant compound) when co-administered with MMP-9 or a biologically active fragment or variant thereof than when administered in the absence of MMP-9 or a biologically active fragment or variant thereof.

The methods and formulations of the present disclosure may be applied to a subject such as a human, non-human primate, or a domesticated or semi-domesticated animal. The subject may be a cow, sheep, goat, pig, horse, dog, cat, rabbit, rat, mouse, or the like. In some embodiments, the subject is a mammal. In some embodiments, the subject is a primate. In some embodiments, the subject is a human.

Pharmaceutical compounds or formulations of the present disclosure may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

The compounds of the present disclosure may be a pharmaceutically acceptable salt. Representative pharmaceutically acceptable salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate, lactate, maleate, methanesulfonate, nicotinate, 2-naphthalenesulfonate, oxalate, pamoate, pectinate, persulfate, picrate, pivalate, propionate, succinate, tartrate, thiocyanate, phosphate, glutamate, bicarbonate, p-toluenesulfonate, and undecanoate.

The antioxidant compounds may be in prodrug form. Prodrugs are derivatives, which convert into the active agent when introduced into the subject in which they are used, by a chemical or biological process in vivo. Suitable prodrugs include, but are not limited to, peptide conjugates of the antioxidant compounds or MMP-9 and esters of the antioxidant compounds or MMP-9.

It is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

All patents and publications referred to herein are expressly incorporated by reference in their entireties. The citation of any publication is for its disclosure prior to the filing date and should not be construed as an admission that the present claims are not entitled to antedate such publication. Further, the dates of publication provided can be different from the actual publication dates which can be independently confirmed.

As used in the specification and appended claims, the terms "a", "an," and "the" include both singular and plural referents, unless the context clearly dictates otherwise. Thus, for example, "a moiety" includes one moiety and plural moieties.

EXAMPLE

In this example, a study was conducted to evaluate the pharmacokinetics of N-acetyl cysteine administered in an intranasal formulation. The study also evaluated the effectiveness on intranasally administered NAC to increase glutathione concentration in the brain.

C13-labelled N-acetyl L-cysteine (purchased from Cambridge Isotope Laboratories) was used to prepare formulations in phosphate-buffered saline (PBS) for the study. The subjects for the study were male Sprague-Dawley rats weighing approximately 250 grams, and 39 animals were separated into four groups, as shown in Table 1. The animals in the study groups were administered either an intranasal (IN) dose or an oral (PO) dose of N-acetyl cysteine via gavage, as shown in Table 1. Group 1 and group 2 were administered one 20 µl, intranasal injection. Group 3 was administered a single oral dose of 500 µL. Group 4 was administered two separate 10 µL intranasal injections (one per nostril).

TABLE 1

| Group | Compound | Rats per Group (N) | Dose Route | Dose Level (mg/kg) | Dosing Solution Conc. (mg/mL) | Delivery Amount (µL) |
|---|---|---|---|---|---|---|
| 1 | Control Group (PBS) | 9 | Nasal (Control) | 0 | 0 | 20 µL/animal |
| 2 | N-acetyl cysteine | 9 | Nasal | 20 | 250 | 20 µL/animal |
| 3 | N-acetyl cysteine | 12 | PO | 20 | 10 | 500 µL |
| 4 | N-acetyl cysteine | 9 | Nasal | 20 | 250 | 10 µL/nostril, 20 µL/animal |

The animals were fasted the night prior to the study and were anesthetized using a cocktail of ketamine/xylazine before administration of the study formulation. The rats were left on their sides for 15 minutes after administration of the study formulation. The animals were observed post administration, and at least once a day, more if deemed necessary, during the pre-treatment and treatment periods for mortality and morbidity. In particular, signs of ill health were based on body weight loss, change in appetite, and behavioral changes such as altered gait, lethargy and gross manifestations of stress.

Three animals from each Group were sacrificed at the established time points (0.5 hour, 1.0 hour and 2.0 hour), and whole brains from the sacrificed animals were collected for analysis. 3 animals from Group 3 were also sacrificed pre-dose and analyzed. The brain samples were stored at −80° C. freezer until sample analysis. Homogenates of the brain samples were prepared and analyzed, and glutathione (GSH) levels in the brain samples were measured by LC/MS.

Figure 1:
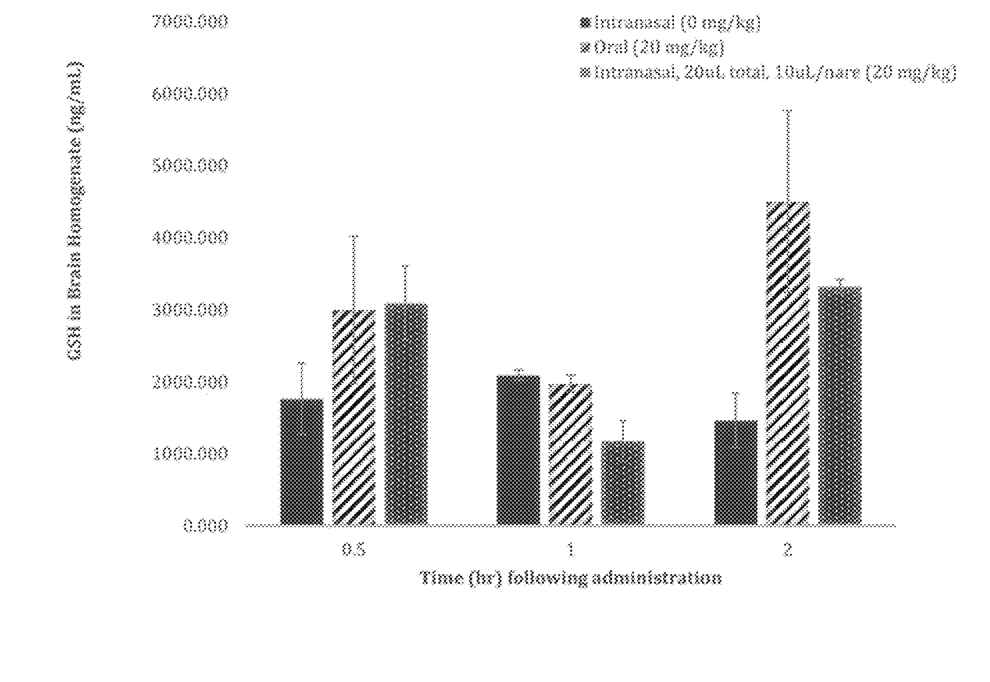
FIG. 1 shows the effect of intranasal delivery of NAC on glutathione in the brain.

Results from the experiments are shown in FIG. 1, which shows the effect of intranasal delivery of NAC on glutathione in the brain. Intranasal N-acetyl cysteine was as effective as oral NAC for raising glutathione levels. Clear trends for increased glutathione, with both intranasal and oral NAC administration are seen 0.5 hours and 2 hours following administration compared to vehicle control (IN PBS). The increased GSH concentration at the 2 hour point in the IN NAC vs IN PBS group is statistically significant (p=0.033, Student's T-test, planned comparison).

Glutathione is a primary endogenous antioxidant and interventions to increase glutathione concentration are thought to be effective in reducing TBI sequelae. Rai et al., BMC Anesthesiol. 2017 Jun. 15; 17(1):81. Orally administered NAC, a glutathione precursor, has been shown to be effective in reducing the symptoms of mild-moderate traumatic brain injury in human patients. Hoffer et al., PLoS One. 2013; 8(1):e54163. However orally administered NAC may cause nausea, vomiting and diarrhea, exacerbating the symptoms from a TBI making it unlikely that a patient will finish a medication if it is required to be taken for 7 days for example. See Chiew et al., Cochrane Database Syst Rev. 2018 February; 2018(2). Oral delivery is also not a viable administration method for all patients, for example for a person who is unresponsive, not capable of swallowing a pill. However, intranasal administration can be applied on an unconscious person and may be an effective treatment option for rapid therapeutic administration. Ouyang et al., Ment Health Clin. 2018 Mar. 23; 7(6):287-289; Fisher et al., Prehosp Emerg Care. 2016 November-December; 20(6): 675-680. Additionally, studies have shown oral NAC having a low blood brain barrier permeability, providing another reason for intranasal delivery. Senol et al., Neurochem Res (2014) 39(4):685-92. Last, intranasal NAC can be administered outside of a clinic unlike IV (another potential route of administration being studied with other therapeutics). Interestingly the example study in this application did not detect an increase in the concentration of isotope labeled NAC in brain tissue following administration, which suggests that NAC conversion to cysteine required for glutathione synthesis likely occurs in the vasculature, followed by cysteine uptake across the blood brain barrier. See Eakin et al., PLoS One. 2014; 9(4): e90617; Zhou et al., J Pharm Sci. 2015 August; 104(8):2619-26.

EXEMPLARY EMBODIMENTS

Exemplary embodiments provided in accordance with the presently disclosed subject matter include, but are not limited to, the claims and the following embodiments:

A. A method of treating a central nervous system (CNS) disorder, the method comprising intranasally administering to a subject an effective amount of at least one antioxidant compound or a pharmaceutically acceptable salt thereof.

A1. The method of embodiment A, wherein the antioxidant compound is selected from the group consisting of N-acetylcysteine (NAC), glutathione, co-enzyme Q-10, superoxide dismutase (SOD), and a combination thereof.

A2. The method of embodiment A or A1, wherein the method further comprises administering to the subject matrix metallopeptidase 9 (MMP-9) or a biologically active fragment or variant thereof.

A3. The method of embodiment A2, wherein matrix metallopeptidase 9 (MMP-9) or a biologically active fragment or variant thereof is intranasally administered to the subject prior to administering the at least one antioxidant compound.

A4. The method of embodiment A to A3, wherein the method further comprises administering to the subject trofinetide, progesterone, neurosteroid, a ghrelin compound, a salt thereof, or a combination thereof.

A5. The method of embodiment A to A4, wherein the central nervous system disease is selected from traumatic brain injury (TBI). Parkinson's disease. Huntington's disease, Alzheimer's disease, stroke, depression, bipolar disorder, and amyotrophic lateral sclerosis (ALS).

A6. The method of embodiment A to A5, wherein the method further comprises administering to the subject an inhibitor of an purinergic receptor selected from the group consisting of P2X4. P2X7, P2Y6, and P2Y12.

A7. The method of embodiment A to A6, wherein the at least one antioxidant is administered in combination with a chitosan loaded nanoparticle, a lipophilic micelle, or a liposomal carrier.

A8. The method of embodiment A to A7, wherein the subject is a human.

B. A method of treating a traumatic brain injury (TBI), the method comprising administering to a subject an effective amount of a pharmaceutical composition comprising at least one pharmaceutical compound and matrix metallopeptidase 9 (MMP-9) or a biologically active fragment or variant thereof.

B1. The method of embodiment B, wherein the pharmaceutical compound is an antioxidant compound selected from the group consisting of N-acetylcysteine (NAC), glutathione, co-enzyme Q-10, superoxide dismutase (SOD), and a combination thereof.

B2. The method of embodiment B1, wherein the pharmaceutical compound is N-acetylcysteine.

B3. The method of embodiment B, wherein the pharmaceutical compound is selected from the group consisting of trofinetide, progesterone, neurosteroid, a ghrelin compound, or a combination thereof.

B4. The method of any one of embodiment B to B3, wherein the MMP-9 comprises a full-length human MMP-9 protein.

B5. The method of embodiment B to B4, wherein the pharmaceutical composition is administered using an intranasal device.

B6. The method of embodiment B to B4, wherein the pharmaceutical composition is administered orally, topically, subcutaneously, or via a transdermal patch.

B7. The method of embodiment B to B6, wherein the pharmaceutical composition is administered from 1 to 30 days.

B8. The method of embodiment B to B7, wherein the method further comprises administering to the subject an inhibitor of a purinergic receptor selected from the group consisting of P2X4. P2X7, P2Y6, and P2Y12.

B9. The method of embodiment B to B8, wherein the method further comprises administering acetaminophen or aspirin to the subject.

B10. The method of embodiment B to B9, wherein the subject is a human.

B11. The method of embodiment B to B10, where the pharmaceutical composition is a topical ointment as a stand-alone therapy or a combination therapy with at least one antioxidant compound or a pharmaceutically acceptable salt thereof.

B12. The method of embodiment B11, wherein the topical ointment further comprises an agent with surfactant qualities such as Vitamin A, B, C, D or E derivatives to help carry the drug through the epithelial layer and/or a cyclodextrin such as hydroxypropyl cyclodextrins (HPbetaCD) to protect the drug while in transit.

C. A pharmaceutical formulation for treating a central nervous system (CNS) disorder comprising at least one antioxidant compound or a pharmaceutically acceptable salt thereof and matrix metallopeptidase 9 (MMP-9) or a biologically active fragment or variant thereof.

C1. The pharmaceutical formulation of embodiment C, wherein the antioxidant compound is selected from the group consisting of N-acetylcysteine (NAC), glutathione, co-enzyme Q-10, superoxide dismutase (SOD), and a combination thereof.

C2. The pharmaceutical formulation of embodiment C or C1 wherein the MMP-9 or a biologically active fragment or variant thereof is a chimeric protein with the MMP-9 catalytic domain fused to a mucoadhesive peptide.

C3. The pharmaceutical formulation of embodiment C to C2, wherein the pharmaceutical formulation further comprises trofinetide, progesterone, a neurosteroid, a ghrelin compound, or a combination thereof.

C4. The pharmaceutical formulation of embodiment C to C3, wherein the pharmaceutical formulation further comprises an inhibitor of a purinergic receptor selected from the group consisting of P2X4. P2X7, P2Y6, and P2Y12.

D. A kit for treating a subject having a central nervous system (CNS) disorder. The kit comprises (a) at least one antioxidant compound or a pharmaceutically acceptable salt thereof, and (b) matrix metallopeptidase 9 (MMP-9) or a biologically active fragment or variant thereof.

D1. The kit of embodiment D, wherein the antioxidant compound is N-acetylcysteine (NAC).

D2. The kit of embodiment D or D1, wherein the kit further comprises an intranasal delivery device.

D3. The kit of embodiment D2, wherein the intranasal delivery device is a sprayer or nebulizer.

E. A method of treating a central nervous system (CNS) disorder, the method comprising intranasally administering to a human subject an effective amount of at least one antioxidant compound or a pharmaceutically acceptable salt thereof, wherein the method comprises administering a total daily dose of the antioxidant compound or salt thereof from about 0.001 to about 100 mg/kg.

E1. The method of embodiment E, wherein the antioxidant compound is selected from the group consisting of N-acetylcysteine (NAC), glutathione, co-enzyme Q-10, superoxide dismutase (SOD), and a combination thereof.

E2. The method of embodiment E or E1, wherein the method further comprises administering to the subject matrix metallopeptidase 9 (MMP-9) or a biologically active fragment or variant thereof.

E3. The method of any of embodiments E, E1 or E2, wherein the method further comprises administering to the subject a non-steroid anti-inflammatory agent.

E4. The method of any of embodiments E to E3, wherein the method further comprises administering to the subject trofinetide, progesterone, neurosteroid, a ghrelin compound, a salt thereof, or a combination thereof.

E5. The method of any of embodiments E to E4, wherein the central nervous system disease is selected from traumatic brain injury (TBI), Parkinson's disease, Huntington's disease, stroke, depression, bi-polar disorder. Alzheimer's disease, and amyotrophic lateral sclerosis (ALS).

E6. The method of any of embodiments E to E5, wherein the method further comprises administering to the subject an agent for enhancing delivery of and/or alleviating odor from the at least one antioxidant compound or salt thereof.

E7. The method of embodiment E6, wherein the agent comprises a cyclodextrin compound in an amount effective to enhance delivery of and/or alleviate odor from the at least one antioxidant compound or salt thereof.

E8. The method of embodiment E6, wherein the agent comprises (2-hydroxypropyl) beta-cyclodextrin (HPBCD), and the agent is administered to the subject before administering the at least one antioxidant compound or salt thereof.

E9. The method of any of embodiments E to E8, wherein the at least one antioxidant compound or salt thereof is administered as a pharmaceutical formulation comprising the at least one antioxidant in combination with one or more sweetening, flavoring or perfuming agents.

E10. The method of any of embodiments E to E9, wherein the at least one antioxidant compound or salt thereof is administered from 1 to 30 days.

F. A kit for treating a subject having a central nervous system (CNS) disorder, the kit comprising: (a) at least one antioxidant compound or a pharmaceutically acceptable salt thereof, and (b) an intranasal delivery device.

F1. The kit of embodiment F, wherein the kit comprises at least one prefilled intranasal delivery device.

F2. The kit of embodiment F or F1, wherein the kit further comprises instructions for using the components of the kit.

F3. The kit of any of embodiments F to F2, wherein the at least one antioxidant compound or salt thereof is contained in a pharmaceutical formulation, and the pharmaceutical formulation is prefilled into the intranasal delivery device; wherein the kit further comprises instructions for using the intranasal delivery device.

F4. The kit of any of embodiments F to F3, wherein the at least one antioxidant compound or salt thereof is contained in a pharmaceutical formulation, and the pharmaceutical formulation is prefilled into a plurality of containers adapted for connection to the intranasal delivery device; wherein the kit further comprises instructions using the components of the kit.

F5. The kit of any of embodiments F to F4, wherein the kit further comprises an outer carrying case for carrying the intranasal delivery device.

F6. The kit of embodiment F5, wherein the outer carrying case is adapted for carrying a plurality of containers and instructions for using the components of the kit.

F7. The kit of any of embodiments F to F6, wherein the kit further comprises a non-steroidal anti-inflammatory agent.

F8. The kit of any of embodiments F to F7, wherein the kit further comprises an agent for enhancing delivery of or and/or alleviating odor from the at least one antioxidant compound or salt thereof, wherein the agent for enhancing delivery of and/or alleviating odor and the at least one antioxidant compound or salt thereof are in separate containers in the kit.

G. A pharmaceutical formulation for intranasal administration comprising at least one antioxidant compound or a pharmaceutically acceptable salt thereof and an agent for enhancing delivery of and/or alleviating odor from the at least one antioxidant compound or salt thereof.

G. The pharmaceutical formulation of embodiment G, the antioxidant compound is selected from the group consisting of N-acetylcysteine (NAC), glutathione, co-enzyme Q-10, superoxide dismutase (SOD), and a combination thereof.

G2. The pharmaceutical formulation of embodiment G or G1, wherein the agent comprises a cyclodextrin compound in an amount effective to enhance delivery of and/or alleviate odor from the at least one antioxidant compound or salt thereof.

G3. The pharmaceutical formulation of any of embodiments G to G2, wherein the agent comprises (2-hydroxypropyl) beta-cyclodextrin (HPBCD).

G4. The pharmaceutical formulation of any of embodiments G to G3, further comprising an analgesic.

G5. The pharmaceutical formulation of any of embodiments G to G4, further comprising trofinetide, progesterone, neurosteroid, a ghrelin compound, a salt thereof, or a combination thereof.

G6. The pharmaceutical formulation of any of embodiments G to G5, further comprising further comprises an inhibitor of a purinergic receptor selected from the group consisting of P2X4, P2X7, P2Y6, and P2Y12.

G7. The pharmaceutical formulation of any of embodiments G to G6, further comprising one or more additives that prevents or slows oxidation of the at least one antioxidant compound or salt thereof.

G8. The pharmaceutical formulation of any of embodiments G to G7, further comprising one or more additives that prevents or slows oxidation of the at least one antioxidant compound or salt thereof.

We claim:

1. A kit for treating a subject having a central nervous system (CNS) disorder, the kit comprising:
   (a) at least one antioxidant compound or a pharmaceutically acceptable salt thereof, wherein the at least one antioxidant compound comprises N-acetylcysteine (NAC),
   (b) an intranasal delivery device, and
   (c) an outer carrying case for carrying the intranasal delivery device, wherein the outer carrying case is adapted to protect the at least one antioxidant compound from severe conditions.

2. The kit of claim 1, wherein the kit comprises at least one prefilled intranasal delivery device.

3. The kit of claim 1, wherein the at least one antioxidant compound or salt thereof is contained in a pharmaceutical formulation, and the pharmaceutical formulation is prefilled into the intranasal delivery device;
   wherein the kit further comprises instructions for using the intranasal delivery device to administer the total daily dose in single or divided doses.

4. The kit of claim 3, wherein the intranasal delivery device is prefilled with an amount of the pharmaceutical formulation to administer the total daily dose for at least 2 days.

5. The kit of claim 3, wherein the intranasal delivery device is prefilled with an amount of the pharmaceutical formulation to administer the total daily dose for at least 7 days.

6. The kit of claim 1, wherein the at least one antioxidant compound or salt thereof is contained in a pharmaceutical formulation, and the pharmaceutical formulation is prefilled into a plurality of containers adapted for connection to the intranasal delivery device;
   wherein the kit further comprises instructions for using the plurality of containers to administer the total daily dose in single or divided doses.

7. The kit of claim 1, wherein the outer carrying case is adapted to be stored in a soldier's backpack.

8. The kit of claim 1, wherein the outer carrying case is adapted for carrying a plurality of containers and instructions for using the components of the kit, wherein each of the containers contains the total daily dose of the at least one antioxidant compound, and
   the instructions are for using each of the containers to administer the total daily dose in a single dose.

9. The kit of claim 1, wherein the kit further comprises an agent for enhancing delivery of or and/or alleviating odor from the at least one antioxidant compound or salt thereof,
   wherein the agent for enhancing delivery of and/or alleviating odor and the at least one antioxidant compound or salt thereof are in separate containers in the kit.

10. The kit of claim 1, wherein the at least one antioxidant compound or salt thereof is contained in a pharmaceutical formulation.

11. The kit of claim 10, wherein the pharmaceutical formulation further comprises an agent for enhancing delivery of the at least one antioxidant compound or salt thereof.

12. The kit of claim 10, wherein the pharmaceutical formulation further comprises an agent for alleviating odor of the at least one antioxidant compound or salt thereof.

13. The kit of claim 10, wherein the pharmaceutical formulation further comprises a cyclodextrin compound.

14. The kit of claim 10, wherein the pharmaceutical formulation further comprises (2-hydroxypropyl) beta-cyclodextrin (HPBCD).

15. The kit of claim 10, wherein the pharmaceutical formulation further comprises an additional antioxidant to prevent NAC oxidation.

16. The kit of claim 10, wherein the pharmaceutical formulation further comprises ethylenediaminetetraacetic acid (EDTA).

17. The kit of claim 1, wherein the outer carrying case is adapted to protect the at least one antioxidant compound from extreme heat and extreme cold.

18. The kit of claim 1, wherein the outer carrying case is adapted for carrying a plurality of containers and instructions for using the components of the kit, wherein each of the containers contains a submultiple of the total daily dose of the at least one antioxidant compound, and
   the instructions are for using more than one of the containers to administer the total daily dose in divided doses.

19. A kit for treating a subject having a central nervous system (CNS) disorder, the kit comprising:
   (a) at least one antioxidant compound or a pharmaceutically acceptable salt thereof, wherein the at least one antioxidant compound comprises N-acetylcysteine (NAC), and
   (b) an intranasal delivery device,
   wherein the kit further comprises a non-steroidal anti-inflammatory agent.

* * * * *